United States Patent [19]
Satake et al.

[11] Patent Number: 5,859,435
[45] Date of Patent: Jan. 12, 1999

[54] CONTENT MEASURING APPARATUS FOR PLANT LEAF

[75] Inventors: Satoru Satake, Tokyo; Nobuhiko Nakamura, Hiroshima, both of Japan

[73] Assignee: Satake Corporation, Tokyo, Japan

[21] Appl. No.: 903,953

[22] Filed: Jul. 31, 1997

[30] Foreign Application Priority Data

Aug. 1, 1996 [JP] Japan .................................. 8-220598
Jul. 30, 1997 [JP] Japan .................................. 9-219252

[51] Int. Cl.$^6$ .................................................. G01N 21/35
[52] U.S. Cl. ............................ 250/341.7; 250/339.01; 250/339.06; 250/339.12; 250/353
[58] Field of Search ........................... 250/341.7, 339.12, 250/339.06, 339.01, 353

[56] References Cited

U.S. PATENT DOCUMENTS

| | | | |
|---|---|---|---|
| 4,429,225 | 1/1984 | Fumoto et al. | 250/353 |
| 4,801,804 | 1/1989 | Rosenthal | 250/341.2 |
| 5,237,178 | 8/1993 | Rosenthal et al. | 250/341.7 |
| 5,254,858 | 10/1993 | Wolfman et al. | 250/339.06 |

FOREIGN PATENT DOCUMENTS 8-15141  1/1996  Japan .

OTHER PUBLICATIONS

Patent Abstracts of Japan, publication No. 08015141A, published Jan. 19, 1996.

*Primary Examiner*—Constantine Hannaher
*Attorney, Agent, or Firm*—Fish & Richardson P.C.

[57] ABSTRACT

A content measuring apparatus has a light source for irradiating near infrared light on a leaf, a light intensity detecting device for receiving transmitted light from the leaf, an operation means for calculating the light absorbance of the leaf from the intensity of transmitted light and computing a content percent of the leaf based on a content percent estimation equation. The light source includes light emitting elements which are disposed so as to have predetermined angles with respect to a diffuse reflectance plate coated with mat paint, a light reflection path which shades direct light from the light emitting elements, is arranged in a vertical direction at a substantial center of the diffuse reflectance plate and conducts the reflected light from the diffuse reflectance plate, light reflection path also being coated with mat paint, and a diffuse transmittance plate which is provided at a light radiating side of the reflected light path for making the reflected light uniform whereby the radiation light from the diffuse transmittance plate is irradiated on the leaf. In fabricating the device, the mechanical process for forming a sphere surface as required in an integration sphere can be dispensed with so that the cost for fabrication is low, and the variations in the light intensity are no larger than those in the integration sphere.

6 Claims, 6 Drawing Sheets

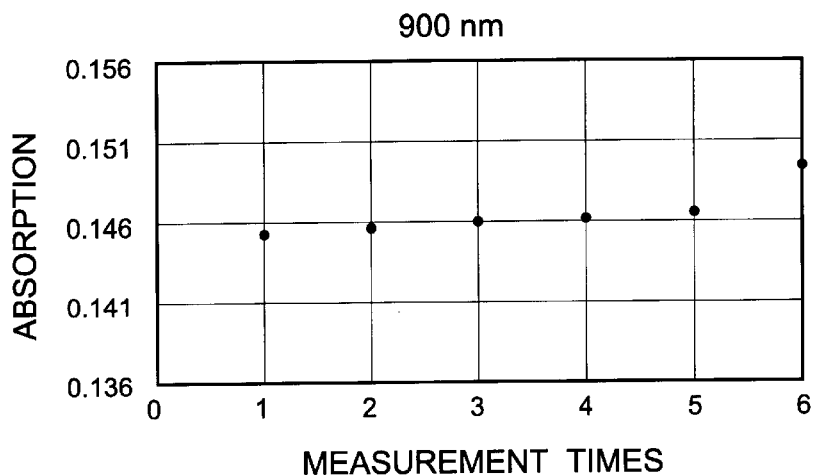
Fig. 7 (1)
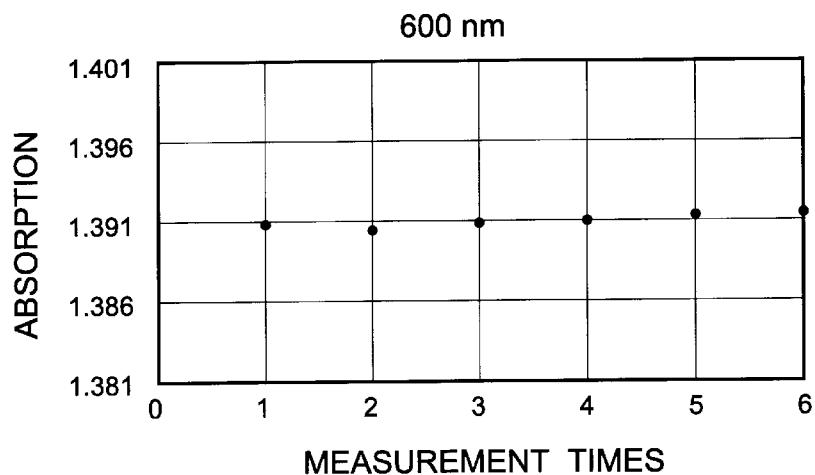
Fig. 7 (2)
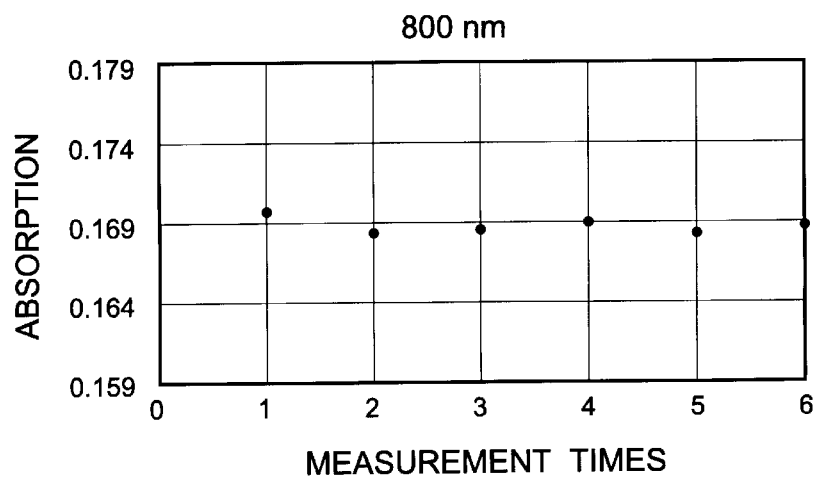
Fig. 7 (3)

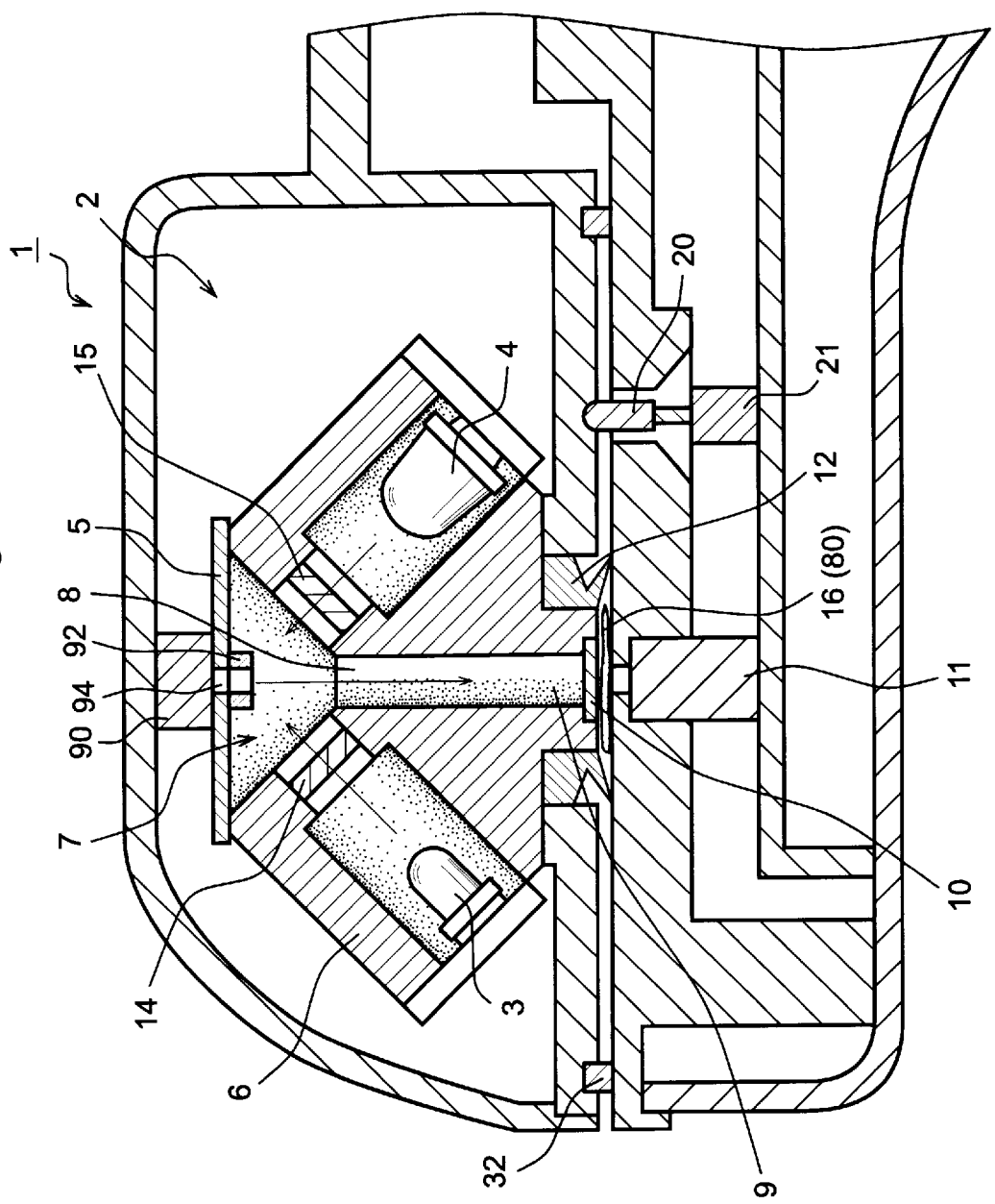

000
CONTENT MEASURING APPARATUS FOR PLANT LEAF

BACKGROUND OF THE INVENTION (1). Field of the Invention

The present invention relates to a content measuring apparatus of a portable type, and more particularly to an apparatus for measuring contents of plant leaf which are in relation to the growth thereof.

(2). Description of the Related Art

Conventionally, the content of nitrogen has been estimated from the content of chlorophyll by such methods as making an assumption of the content of nitrogen by the comparison of the color of a leaf with a color scale, or measuring the content of chlorophyll contained in a leaf by calculating the light intensity of the red rays and the infrared rays from the light transmitted upon the light being irradiated on the leaf to be measured. Also, the fertilizer application rate has been judged so as to be in accord with the estimated content of nitrogen and the plant growing periods. Particularly, in the case of rice crop, the subsequent fertilizer application time and rate judged from the estimated nitrogen content are important points in order to ensure that the rice plant does not undergo the falling down and yet the best yield of grains is achieved.

In using the method wherein the color of the leaf is compared with the color scale, the problems are not only in the requiring of experiences but also in frequent incorrect results of judgment because the color of the leaf to the human eyes may be different depending on any weather conditions or the location and the direction of the sun light, on any differences in observation, that is, whether it is partial observation or total observation, and on the observation angle. However, because this prior art method is simple and that the color scale is inexpensive, it is true that its utilization factor is high.

A chlorophyll measuring device which substitutes for the color scale has been developed. The measuring principle of a typical chlorophyll meter may be apparent from FIG. 1 in which the leave 50 to be measured is subjected to the irradiation of light from a light source 51 and the light transmitted is measured and in which, by a dichroic mirror 52, the measurement is made of the intensity of transmitted light of the red light region (received by a light receiving diode 53) which is affected by the chlorophyll content and the intensity of the transmitted light of the infrared light region (which is received by a light receiving diode 54) which is not affected by the chlorophyll content. By calculating the light intensity difference therebetween, the estimation is made of the chlorophyll concentration per unit area without the leaf being destructed. However, in practice, the estimation of the nitrogen concentration is premised on the assumption that the chlorophyll concentration and the nitrogen concentration are on a proportional relationship, and this estimation is being utilized for the fertilizer application rate to a plant.

One of the inventors together with two others have developed and proposed in Japanese Patent Application Kokai Publication No. Hei 8-15141 a content percent measuring device for leaves of a plant with which the nitrogen content therein can be measured in a simple manner. This is explained with reference to FIG. 2. Shown in FIG. 2 is an optical measurement section 60 which is the main constituent element of the content percent measuring device for leaves of a plant, in which the light emitting means 62 for irradiating near infrared light of a predetermined wavelength onto a leaf 61 to be measured comprises a near infrared light emitting element 63 which is constituted by an element such as a light emitting diode (LED), and a narrow band filter 64 which permits the passing of only the near infrared light of a predetermined wavelength. There are provided leave holding means 66A and 66B which hold between them in planar the leaf 61 such that the near infrared light may be uniformly irradiated on the surface of the leaf 61 and which are provided with measuring windows 65A and 65B for measuring the transmitted light and the reflected light from the leaf 61. The measuring window 65B of the leave holding means 66B and the light emitting means 62 are communicated with each other by an integration sphere 67. That is, the light emitting means 62 is fixed to the integration sphere 67 so as to permit the light to be irradiated and dispersed within the integration sphere 67, and the integration sphere 67 is provided with an opening 68 which communicates with the measuring window 65B and an opening 70 at which a reflected light receiving means 69 constituted by a silicon photodiode is fixed.

As to the operation of the content percent measuring device for leaves constructed as above, the near infrared light irradiated from the light emitting means 62 is dispersed in the integration sphere 67 and is then irradiated on the surface of the leaf 61 from the measuring window 65B. Also, the light reflected from the leave 61 is dispersed in the integration sphere 67 and then is received by the reflected light receiving means 69. Further, the portion of the near infrared light that has been irradiated on the leaf 61 and transmitted therethrough is received as transmitted light by a transmitted light receiving means 71 which is constituted by a silicon photodiode fixed at the measuring window 65A side of the leave holding means 66.

In the use of the integration sphere having the above configuration, the advantages are that it is possible to increase the light intensity of the light source and that, in the case where the number of wavelengths used for measuring has become large for securing the measurement precision, the light of all the wavelengths is uniformly irradiated on the leave irrespective of the light emitting locations. However, in fabricating the integration sphere 67, its inside is given a spherical treatment, its spherical surface Is given a matte treatment and, thereafter, it is finished by gold plating so that the fabrication cost is unavoidably high.

SUMMARY OF THE INVENTION

An object of the invention is to overcome the problems existing in the prior art, and to provide an improved content measuring apparatus in which, as compared with the use of an integration sphere, the mechanical processing for sphere as required in the case of the fabrication of the integration sphere can be dispensed with and in which the light source is such that any variations in the light intensity are not larger when compared with those in the integration sphere and are to the extent that they have no adverse effects to the measurement precision.

According to the invention, there is provided a content measuring apparatus for a plant leaf having a light source section for irradiating near infrared light of a predetermined wavelength on a sample leaf to be measured, a light intensity detecting device for receiving at least transmitted light from the sample leaf, and an operation means for determining a content percent estimation equation based on the light absorbance obtained by irradiating the near infrared light on a reference object whose content percent has been known, and computing a content percent for a specific content of the sample leaf based on the content percent estimation equation and the light absorbance of the sample leaf, the light source section comprising:

a diffuse reflectance plate;

a plurality of light emitting elements each having a light axis directed to the diffuse reflectance plate with a predetermined inclination angle with respect to the diffuse reflectance plate;

a reflection light path for conducting the reflected light from the diffuse reflectance plate with direct light from the plurality of light emitting elements being shaded, the reflection light path arranged perpendicularly with respect to a surface of the diffuse reflectance plate at a substantial center of the diffusion reflection plate;

a diffuse transmittance plate arranged at a irradiating side of the reflection light path, for making the reflection light uniformly irradiate on the sample leaf; and a light controller for appropriately controlling the plurality of light emitting elements.

It is most general for a plurality of the light emitting elements to employ a plurality of light emitting diodes having respectively different specific wavelength peaks, and the provision of a plurality of narrow band filters in combination with the plurality of the light emitting elements enable the rays to have sharper wavelengths. The light emitting elements may also be realized by a combination of a halogen lamp and a narrow band filter. The diffuse reflectance plate may be formed such that, on a plate which does not permit the light to transmit, a coating is made with mat paint which has preferably high weather resistant property (for example, Product name: Flon coat (fluorine-containing resin paint), Product name: Polyzine (polyester resin paint) both manufactured by KAWAKAMIPAINT MFG. CO., LTD. in Japan) so that the light may be defuse-reflected without being attenuated or absorbed. The diffuse reflectance plate may also be realized by making the mirror surface a ground glass surface on which the light is diffuse-reflected. Further, a more significant effect can be obtained when the reflected light path is coated with a diffuse-reflecting coating material such as mat paint. Also, the effect is more significant if the diffuse transmittance plate is formed by a milk-white glass so that the light may be transmitted while being diffused and the diffuse transmittance plate may have uniform brightness at the radiating surface. The diffuse transmittance plate functions such that the light incident on the diffuse transmittance plate does not reflect to the diffuse reflectance plate side and also that any transmittance loss due to the diffuse transmittance plate is made minimum.

BRIEF DESCRIPTION OF THE DRAWINGS

The above and other objects, features and advantages of the present invention will be apparent from the following description of preferred embodiments of the invention explained with reference to the accompanying drawings, in which:

FIGS. 7(1), 7(2) and 7(3) are graphs showing the results from the measurement of a sample leaf by the apparatus according to the invention; and FIG. 8 is a diagrammatic sectional view showing, in a partly broken view, a modified apparatus according to the invention.

PREFERRED EMBODIMENT OF THE INVENTION

Figure 5:
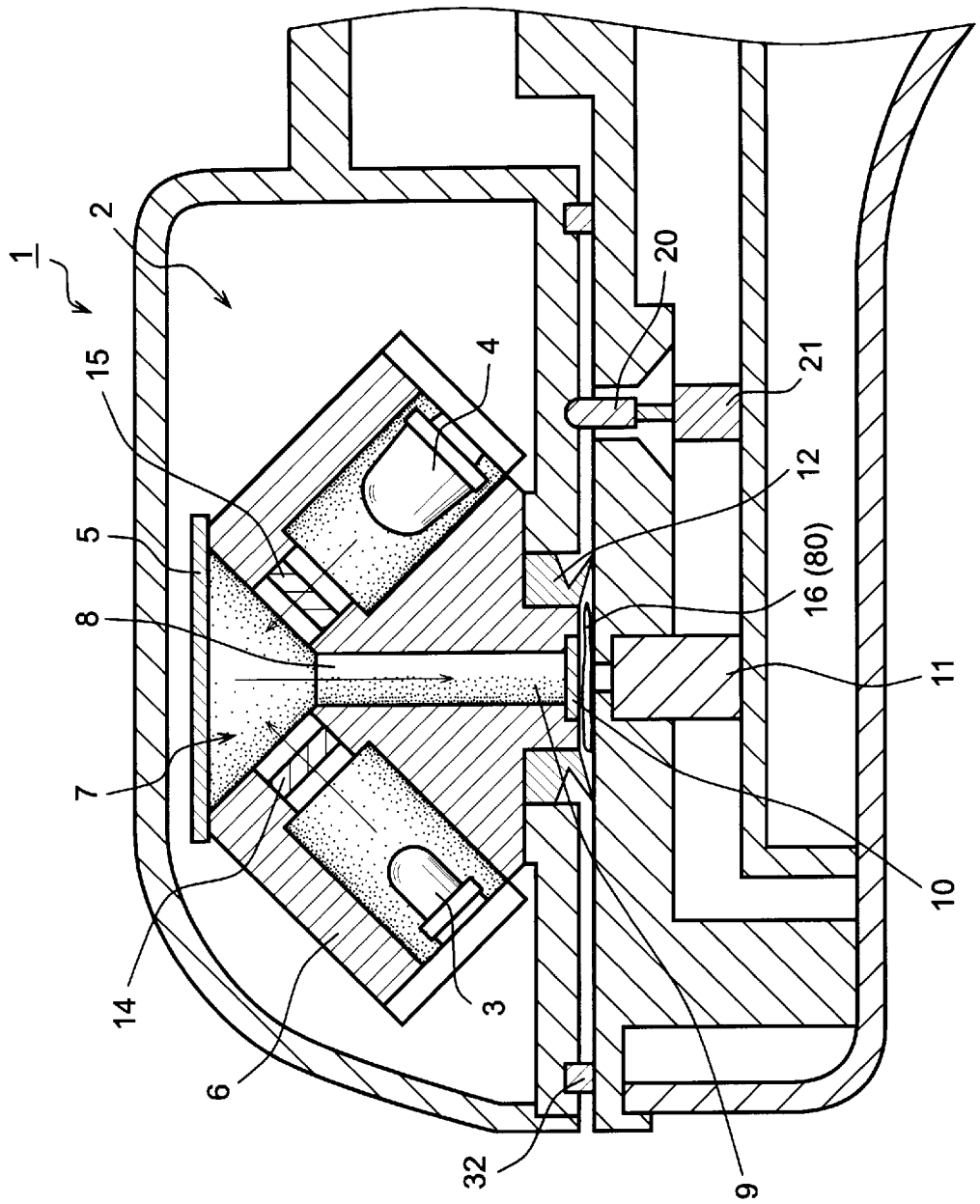
FIG. 5 is a diagrammatic sectional view of a main portion of the content measuring apparatus according to the invention.

Now, a preferred embodiment of the invention is explained with reference to FIG. 5. The preferred embodiment relates to a content measuring apparatus in which the calculation is made of the light absorbance obtained from the light transmitted and received from a plant leaf after irradiating the near infrared light of a predetermined wavelength on the leaf and the computation is made of specific contents in the leaf such as a nitrogen content by using an estimated content equation prepared in advance and the above mentioned light absorbance.

At a light source section 2 of the content measuring apparatus 1, there are provided two light emitting diodes 3 and 4 and, above the light source section 2, there is provided a diffuse reflectance plate 5. The light source section 2 includes a block 6 formed such that the light emitting diodes 3 and 4 may be positioned at locations at which the light from the light emitting diodes 3 and 4 is incident at a predetermined angle with respect to the diffuse reflectance plate 5. At the upper part of the block 6, there is provided a cone-shaped opening 7 which has the diffuse reflectance plate 5 with the reflecting surface facing downwardly.

In the block 6, in a vertical direction at a center portion of the diffuse reflectance plate 5, that is, at a center portion of the cone-shaped opening 7, there is provided a reflected light path 8 which shades the direct light from the light emitting diodes 3 and 4 and conducts the reflected light from the diffuse reflectance plate 5. At the radiating side 9 of the reflected light path a, that is, underneath the block 6, there is provided a diffuse transmittance plate 10 which makes the reflected light uniform.

At a location opposite to the diffuse reflectance plate 5, there is provided a light intensity detection device 11 including a light receiving element, which receives the transmitted light from the diffuse transmittance plate 10. Normally a leaf to be measured is sandwiched between the diffuse transmittance plate 10 and the light intensity detection device 11. In this embodiment, the leaf 16 is sandwiched and the transmitted light of the leaf is detected by the light intensity detection device 11.

With the device arranged as above, the light from the light emitting diodes 3 and 4 is irradiated on the diffuse reflectance plate 5 and is irregularly reflected by the diffuse reflectance plate 5 and is also irregularly reflected between the diffuse reflectance plate 5 and the cone-shaped walls of the block 6. That is, it is enabled to create the irregularly reflected state which approximates an ideal state obtained by the integration sphere, and the reflected light from the diffuse reflectance plate 5 results in the intensity of the light source that is stable irrespective of the locations of the light emitting diodes 3 and 4. The portion of the reflected light from the diffuse reflectance plate 5 that has irregularly been reflected towards the center of the cone-shaped opening 7 is conducted towards the light radiating side 9 along the reflected light path 8 and further the light that has been incident on the diffuse reflectance plate 10 is irradiated on the leaf 16 as uniform light in a transmitting plane while being diffused in the diffuse transmittance plate 10.

In the device explained above, the light from the light emitting diodes 3 and 4 is not directly irradiated on the leaf but is sufficiently diffuse-reflected by the irregular reflection to occur between the diffuse reflectance plate 5 and the cone-shaped opening 7 so that the reflected light intensity from the diffuse reflectance plate 5 is substantially uniform at any locations of the reflection surface irrespective of the locations of the light emitting diodes 3 and 4. Further, according to the invention, since the light is conducted by the reflected light path 8 and is diffused again by the diffuse transmittance plate 10 arranged at the light radiating side 9, the light that is to be irradiated on the transmitting surface of the diffuse transmittance plate 10 is enabled to be irradiated uniformly in a transmitting plane. That is, the light intensity in the transmitting plane of the diffuse transmittance plate results in irradiating the leaf uniformly at any locations so that a problem of variations in the measured values caused by the variations in the intensity of the light irradiated on the leaf has been solved.

Also, since the mat paint coating is provided on the diffuse reflectance plate 5 and on the reflected light path 8 and the reflected light is irregularly reflected at the respective surfaces, the light becomes the diffused light without concentrating at any one location. In this way, any influence from the intensity variations depending on locations of the light emitting diodes 3 and 4 is eliminated, which is a very significant meritorious effect. Further, where the diffuse transmittance plate 10 is formed by a milk-white glass (opal glass), the transmitted light to diffused within the diffuse transmittance plate 10 so that, even when the light is incident thereon with an inclination to some extent, the intensity of the light irradiated from the diffuse reflectance plate 10 is uniform at the irradiating plane of the diffuse transmittance plate 10 and this is also a significant meritorious effect.

In the above explained embodiment wherein the transmitted light from the leaf is received, a reflected light detecting means 90 for receiving the reflected light from the leaf may further be provided, as shown in FIG. 8, on a back surface of the diffuse reflectance plate 5 which has an opening 94 therein, whereby absorbance of the leaf can be measured more precisely.

Figure 1:
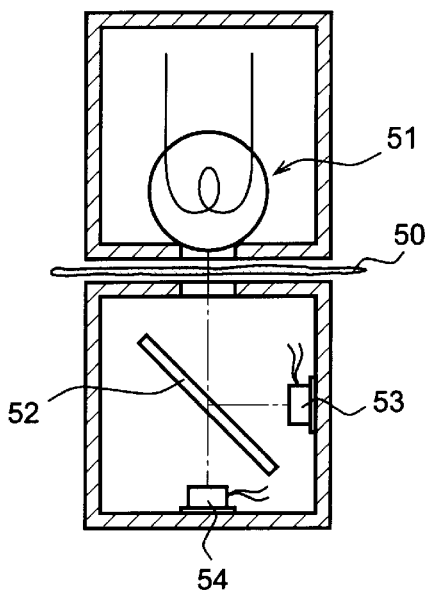
FIG. 1 is a diagrammatic sectional view of a typical conventional chlorophyll meter.
Figure 2:
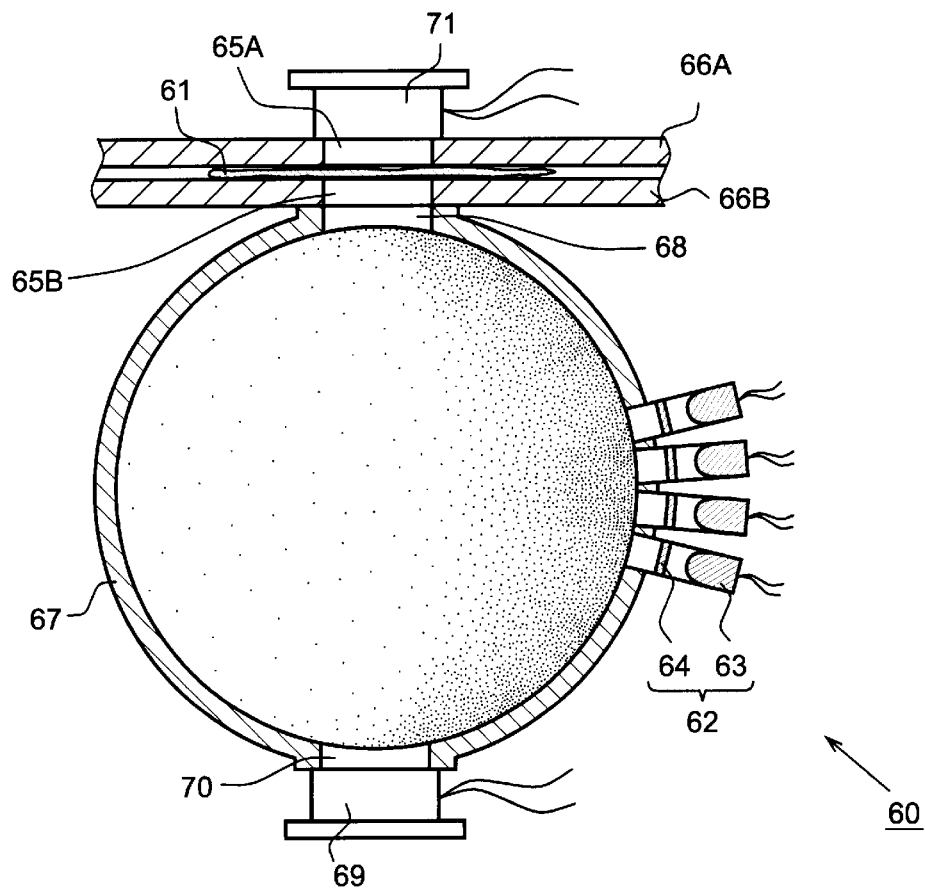
FIG. 2 is a diagrammatic sectional view of an optical measuring section of a conventional content percent measuring device.
Figure 3:
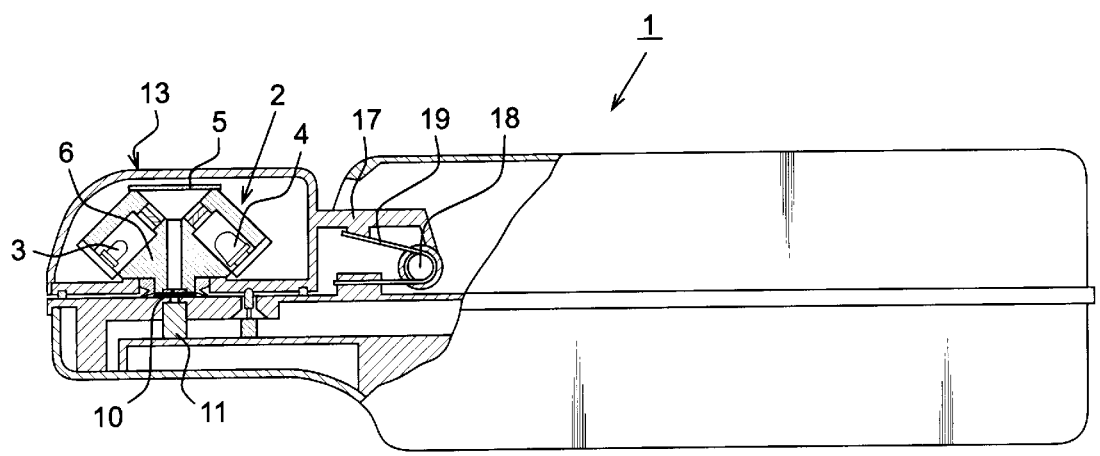
FIG. 3 is a diagrammatic sectional view showing, in a partly broken view, a main portion of the content measuring apparatus according to the invention.
Figure 4:
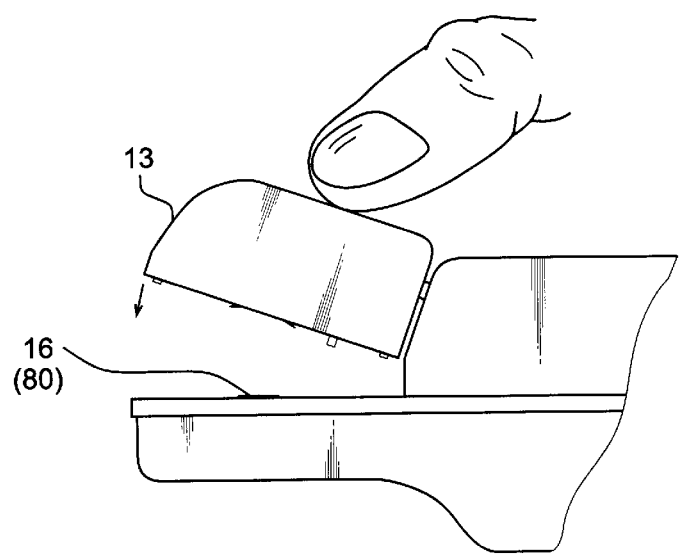
FIG. 4 is a side view of the apparatus in a use state according to the invention.

Now, the preferred embodiment of the invention is explained in detail with reference to FIGS. 3 to 6. Shown in each of FIGS. 3 and 5 is a sectional view, partially broken away, of main portions of a content measuring apparatus of a portable type. In the arrangements of FIGS. 3 and 4, a main body 13 is provided, at its upper part, with a light source section 2 and, at its lower part, with a photodiode (not shown) as a light intensity detection means 11. The light source section 2 is provided with a plurality of light emitting diodes (LEDs) 3 and 4 as light emitting elements which have different nominal wavelength peaks in the same circumference, and the LEDs 3 and 4 are provided with narrow band filters which respectively have different wavelength passing bands. The wavelength bands are from 600 nm to 1100 nm and, from these wavelength bands, the narrow band filters 14 and 15 of predetermined specific wavelengths that relate to the contents to be sought are selected. The light from each of the LEDs 3 and 4 becomes the light of a specific wavelength by the narrow band filters 14 and 15 and then is incident on the diffuse reflectance plate 5 which reflect the light. For the diffuse reflectance plate 5, a block 6 is formed such that the rays from each of the LEDs 3 and 4 are incident on the diffuse reflectance plate 5 with an incident angle being substantially the same or constant.

The light reflected from the diffuse reflectance plate 5 enters the reflected light path 8 provided at the center of the block 6 and is incident on the diffuse transmittance plate 10 provided at the light radiating side 9 of the reflected light path 8. The diffuse reflectance plate 10 is provided vertically with respect to the optical axis of the reflected light path 8 and is formed by a circular ground glass or milky-while glass. The diffuse transmittance plate 10 may be one in which the ground glass surface is formed at either the light radiating side 9 or the side with the leaf 16, or one in which the ground glass surfaces are formed on both the sides. The opening 7 and the reflected light path 8 in the block 6 may be formed using, for example, a solid aluminum or the inside surface of aluminum may be given a matte treatment. However, the same effect at a lower cost can be obtained when the mat paint coating having high weatherability explained above is used.

While repeating the reflection and diffusion in the space surrounded by the opening 7 and the reflected light path 8 as well as the diffuse reflectance plate 5, the light goes out from the reflected light path 8, and the light transmitted through the diffuse transmittance plate 10 is incident on the light intensity detection device 11 through the leaf 16. The numeral 32 depicts a ring-shaped spacer 32 which provides a space in which the sample leaf 16 can be placed between the light intensity detecting device 11 and the diffuse transmittance plate 10.

Further, the light intensity detecting device 2 is provided, at its upper periphery, with an upper lid 13, and an arm 17 which extends from the upper lid 13 is pivotally supported by the axis 18. A coil spring 19 is provided to the axis 18 so that the upper lid 13 is constantly urged upwardly. That is, as seen from FIG. 4, the measuring operation is ready when the leave 16 is inserted into a measuring location and the upper lid 13 is pressed down. When the upper lid 13 is pressed down and a depression projection 20 (see FIG. 5) that is provided under the upper lid 13 in turn presses down a micro-switch provided at an opposite location, the detection is made that the upper lid 13 has been pressed down. This is the timing when the measuring operation (detection of the irradiated light and measuring of the light intensity) is made. Preferably a resilient cover 12 (also see FIG. 5) of a ring-shape is provided so as to surround the diffuse transmittance plate 10, and the function of this cover 12 is, upon the upper lid 13 being pressed down, to press and hold the sample leaf 16 and to shade the light from the outside.

Figure 6:
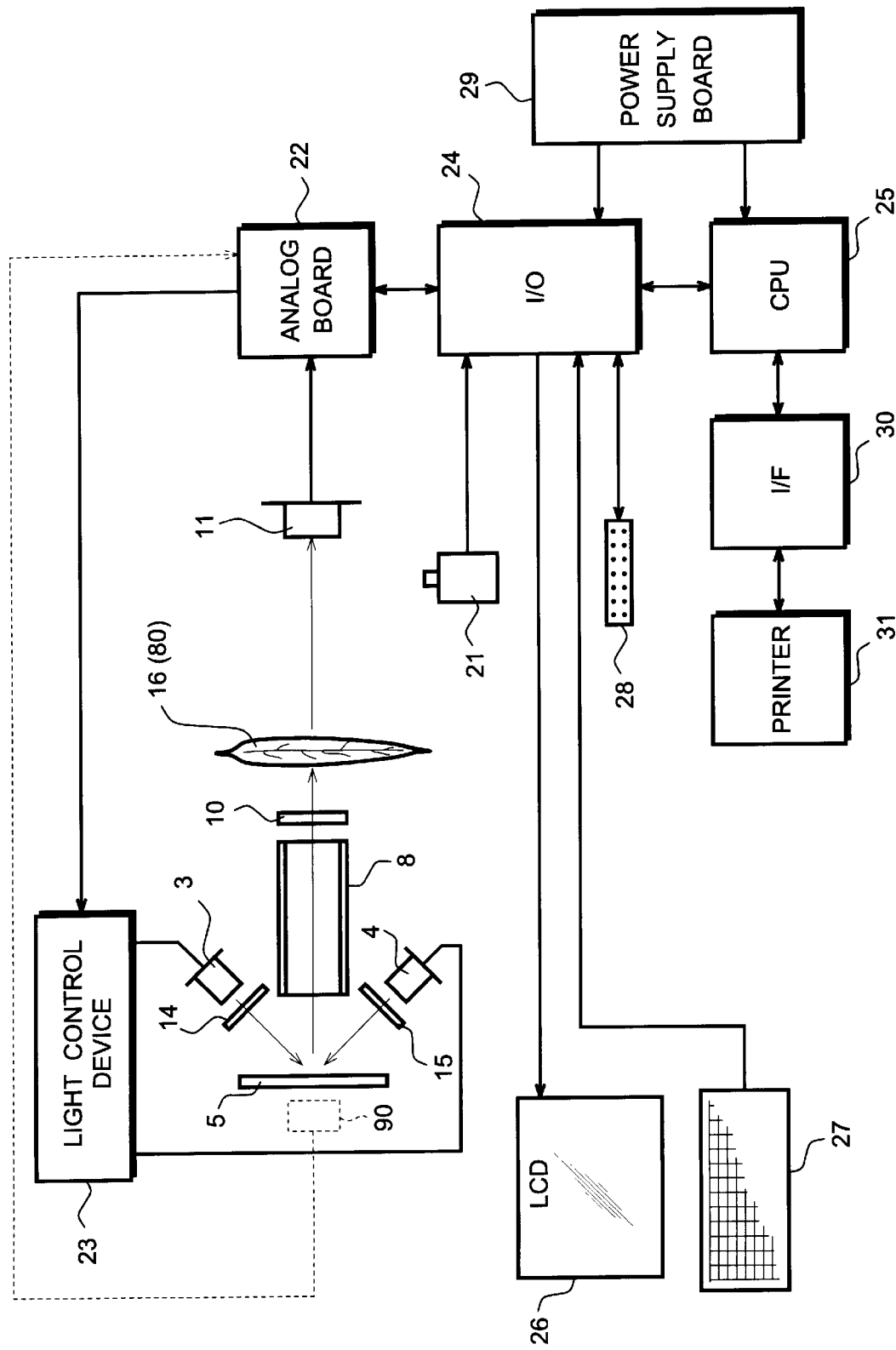
FIG. 6 is a block diagram showing signal processing in the apparatus according to the invention.

Next, with reference to a block diagram of FIG. 6, the content measuring apparatus 1 is explained. The intensity of the light transmitted through the sample leaf 16 which intensity has been detected by the measuring section constituted by the light source section 2 and the light intensity detecting device 11 is converted to an analog signal by the light intensity detecting device 11 and is communicated to an analog board 22. The LEDs 3 and 4 are connected a light control device 23. At the analog board 22, the conversion is made either from an analog signal to a digital signal (A/D conversion) or from a voltage to a frequency (V/F conversion). The converted signal is inputted to a CPU board 25, the function of which includes that of an operation control device, through an I/O board. The I/O board 24 is provided with a liquid crystal display (LCD) 26 which displays measured results, operation results or operation instructions, a keyboard 27 with which the input is made for initial data or various operations, a connecting port 28 of RS232C with which the data is inputted/outputted to and from external devices, and various switches. A power supply board 29 is connected to the CPU board 25 and the I/O board 24 for supplying power thereto. Also, the printer 31 is connected to the CPU board 25 through a printer I/F board 30.

The explanation hereunder relates to the operation of the content measuring apparatus 1 arranged as explained above. First, the standard or reference sample 80 prepared in advance based on the known content percents is placed and measured in the content measuring apparatus 1 and, at the CPU board 25, the content percent estimation equation is drawn based on the absorbance of the standard sample and the actual content percent of the standard sample at the time when the near infrared light is irradiated thereon. This equation is stored in the CPU board 25 which has a storing function.

Then, the standard sample is taken out from the content measuring apparatus 1 and, when the sample leaf 16 is inserted and the upper lid 13 is pressed down, the switch 21 acts and the light emission signal is transmitted to the light source section 2 from the CPU board 25 through the light control device 23 and the light is irradiated onto the leaf from the LEDs 3 and 4 in the light source section 2. The light emitted from the LEDs 3 and 4 results in the specific wavelength of the near infrared region due to the operation of the narrow band filters 14 and 15 and, while repeating the reflection and diffusion, arrives at the light intensity detecting device 11 from the diffuse transmittance plate 10 so that the light is irradiated on the sample leaf 16 in the same extent of uniformity as with the integration sphere.

Upon the light being irradiated on the sample leaf 16, the transmitted light and the reflected light therefrom are received as signals by the light intensity detection device 11 and the received signals are communicated to the analog board 22 for the A/D conversion. At the analog board 22, the A/D conversion is made and the result is inputted to the CPU board 25, which includes the function of an operation control device, through I/O board 24. At the CPU board 25, the light transmittance rate or the light absorbance is calculated based on the transmitted light or the reflected light from the sample leaf 16.

After the calculation of the light absorbance of the sample leaf 16, the value of the light absorbance is substituted for the content percent estimation equation stored in advance, and finally the content percent sought for by the operator is calculated.

In the CPU board 25, it is possible to provide a light source lighting routine with which the lighting from the LEDs 3 and 4 may be repeated with predetermined intervals. With this light source lighting routine, the LEDs 3 and 4 each having a different nominal wavelength peak are caused to be lit, and the transmitted light intensity is measured of the sample leaf 16 on a wavelength to wavelength basis. In this way, the measuring precision of the transmitted light intensity of the sample leaf 16 can be improved, and also the measuring precision of the light absorbance of the sample leave 16 can be improved.

FIGS. 7(1), 7(2) and 7(3) are graphs showing verified variations in the values obtained from the measurement of the same sample leaf 16 a plurality of times using the content measuring apparatus described above. FIG. 7(1) shows the values obtained when the wavelength of the irradiated light was 900 nm, FIG. 7(2) shows the values when the same was 600 nm, and FIG. 7(3) shows the values when the same was 800 nm. The same spot of the same sample leaf was measured 6 times and, at each time, the sample leaf was re-inserted for being held by the device. The result showed that there was almost no variation in the measured values and that the values were as constant as those with the integration sphere. When the irradiated light is not uniform in a plane of irradiation, that is, when the light intensity is not uniform in the plane of irradiation unlike in the case where the integration sphere is used, the measuring of even the same spot of the re-inserted sample leave resulted in a different value each time the measurement is made, thus the variations being present in the measured values.

The measurement of absorbance in the device of the invention is not limitative to the measurement of the transmitted light from the leaf. As illustrated in FIG. 8, in addition to the measurement of transmitted light, the reflected light may be measured so as to enhance the measuring precision of absorbance. More specifically, the reflected light receiving means 90 is provided on a back surface of the diffuse reflectance plate 5 having an opening 94 therein, at a portion of a substantial center of the reflectance plate 5. The opening 94 at the reflection light path 8 side is provided with a light shading member 92 which prevents the light from the light emitting diodes 3 and 4 from directly entering the reflected light receiving means 90. It is needless to say that the detection signal from the reflected light receiving means 90 is forwarded to the analog board 22 shown in FIG. 4 as is the same for the detection signal from the transmittance light detection means 11.

In the content measuring apparatus of the invention described above, when the light is irradiated to the diffuse reflectance plate, the light is diffuse-reflected by the diffuse reflectance plate and the opening thus losing Its directivity, and the light enters the reflected light path and, while being reflected and diffused once or a plurality of times, the light arrives at the diffuse transmittance plate. Further, at the diffuse transmittance plate, the light is again diffused in the diffuse reflectance plate and is irradiated on the sample leaf from the diffuse reflectance plate. Therefore, without causing the light intensity at the light source to be reduced, it is made possible to irradiate the light on the sample leaf in the same extent of uniformity as with the integration sphere. Further, as compared with the case when the integration sphere is used, since the mechanical process for forming sphere in the integration sphere can be dispensed with, the cost of fabricating the device according to the invention is low.

Also, a plurality of the light emitting diodes are provided such that their light is incident on the diffuse reflectance plate with the same angle so that, where a plurality of the light emitting diodes are provided for securing the measuring precision, the distance to the diffuse reflectance plate from each of the light emitting diodes respectively having different wavelengths becomes the same so that the sample leaf can be irradiated uniformly by the light from all of the light emitting diodes.

While the invention has been described in its preferred embodiments, it is to be understood that the words which have been used are words of description rather than limitation and that changes within the purview of the appended claims may be made without departing from the true scope of the invention as defined by the claims.

What is claimed is:

1. A content measuring apparatus for a plant leaf having a light source section for irradiating near infrared light of a predetermined wavelength on a sample leaf to be measured, a light intensity detecting device for receiving at least transmitted light from said sample leaf, and an operation means for determining a content percent estimation equation based on the light absorbance obtained by irradiating the near infrared light on a reference object whose content percent has been known, and computing a content percent for a specific content of the sample leaf based on said content percent estimation equation and the light absorbance of said sample leaf, said light source section comprising:

- a diffuse reflectance plate;
- a plurality of light emitting elements each having a light axis directed to said diffuse reflectance plate with a predetermined inclination angle with respect to said diffuse reflectance plate;
- a reflection light path for conducting the reflected light from said diffuse reflectance plate with direct light from said plurality of light emitting elements being shaded, said reflection light path arranged perpendicularly with respect to a surface of said diffuse reflectance plate at a substantial center of said diffusion reflection plate;
- a diffuse transmittance plate arranged at a irradiating side of said reflection light path, for making the reflection light uniformly irradiate on said sample leaf; and
- a light controller for appropriately controlling said plurality of light emitting elements.

2. The content measuring apparatus for a plant leaf according to claim 1, in which surfaces of said diffuse reflectance plate and said reflected light path are coated with mat paint.

3. The content measuring apparatus for a plant leaf according to claim 1, in which said diffuse transmittance plate is a milk-white glass plate.

4. The content measuring apparatus for a plant leaf according to claim 1, in which said diffuse transmittance plate has a ground glass surface at least on one side thereof.

5. The content measuring apparatus for a plant leaf according to claim 1, in which said specific component of said sample leaf is nitrogen.

6. The content measuring apparatus for a plant leaf according to claim 1, further comprising a reflected light intensity detecting means for receiving reflected light from said sample leaf, said reflected light intensity detecting means being arranged on a back surface of said diffuse reflectance plate at a substantial center thereof opposing to said reflection light path.

* * * * *

UNITED STATES PATENT AND TRADEMARK OFFICE
CERTIFICATE OF CORRECTION

PATENT NO. : 5,859,435

DATED : January 12, 1999

INVENTOR(S) : Satoru SATAKE, Nobuhiko NAKAMURA

It is certified that error appears in the above-identified patent and that said Letters Patent is hereby corrected as shown below:

Column 2, line 43, change "Is" to --is--;

Column 4, line 43, change "path a" to --path 8--; and

Column 8, line 32, change "Its" to --its--.

Signed and Sealed this

First Day of June, 1999

Attest:

Q. TODD DICKINSON

*Attesting Officer*  *Acting Commissioner of Patents and Trademarks*